US012576202B2

(12) United States Patent (10) Patent No.: US 12,576,202 B2
Schmal et al. (45) Date of Patent: Mar. 17, 2026

(54) INSERT FOR A CENTRIFUGE ROTOR HAVING LUBRICANT-FREE BEARING

(71) Applicant: Andreas Hettich GmbH & Co. KG, Tuttlingen (DE)

(72) Inventors: Thomas Schmal, Emmingen (DE); Marcellus Geiselmann, Tuttlingen (DE); Klaus-Guenter Eberle, Tuttlingen (DE)

(73) Assignee: ANDREAS HETTICH GmbH CO. KG, Tuttlingen (DE)

( * ) Notice: Subject to any disclaimer, the term of this patent is extended or adjusted under 35 U.S.C. 154(b) by 762 days.

(21) Appl. No.: 17/916,350

(22) PCT Filed: Mar. 29, 2021

(86) PCT No.: PCT/EP2021/058069
§ 371 (c)(1),
(2) Date: Sep. 30, 2022

(87) PCT Pub. No.: WO2021/198128
PCT Pub. Date: Oct. 7, 2021

(65) Prior Publication Data
US 2023/0149618 A1 May 18, 2023

(30) Foreign Application Priority Data
Apr. 2, 2020 (DE) ..................... 10 2020 109 189.3

(51) Int. Cl.
*A61M 1/36* (2006.01)
*A61M 1/38* (2006.01)

(52) U.S. Cl.
CPC ............ *A61M 1/3693* (2013.01); *A61M 1/38* (2013.01)

(58) Field of Classification Search
CPC .... A61M 1/3693; A61M 1/38; A61M 1/0209; A61M 1/0272; A61M 1/3696;
(Continued)

(56) References Cited

U.S. PATENT DOCUMENTS 1,195,756 A * 8/1916 Wingquist .............. F16C 19/18
384/523
3,559,880 A 2/1971 Naito
(Continued)

FOREIGN PATENT DOCUMENTS

DE 10065283 A1 7/2002
DE 202019104978 U1 10/2019
WO 02053292 A2 7/2002

OTHER PUBLICATIONS

PCT Written Opinion dated Jul. 2, 2021 in counterpart PCT Application No. PCT/EP2021/058069 (5 pages in English).
(Continued)

*Primary Examiner* — Claire X Wang
*Assistant Examiner* — Shuyi S. Liu
(74) *Attorney, Agent, or Firm* — Juan Carlos A. Marquez; Marquez IP Law Office, PLLC

(57) ABSTRACT

An insert (10) for a rotor (14), which rotates about a rotor axis (12), of a centrifuge (16) incorporating a housing (30) having at least one container for bags, in particular blood bags, that comprises a slider (66) that cooperates with a drive, a rotatable spindle nut (62) and a spindle (64), wherein the spindle nut (62) is rotatably mounted in the housing (30) and connected to the drive, and the spindle (64) is translationally slidably mounted in the spindle nut (62) and connected to the slider (66). The slider (66) is arranged in the container and acts on the bag in a predetermined manner.
(Continued)

The spindle (64) moves between a starting position and an operating position, wherein the spindle nut (62) is rotatably mounted in the housing (30) via at least one bearing (60). The bearing (60) is formed by a lubricant-free bearing (60) having an outer bearing ring in contact with the housing and a bearing ring in contact with the spindle nut (62).

20 Claims, 4 Drawing Sheets

(58) Field of Classification Search
CPC ................. A61M 1/029; B04B 5/0428; B04B 2005/0435; B04B 5/0442; B04B 2005/0478; B04B 5/0407; B04B 2011/046; B04B 5/04; B04B 7/00; B04B 9/00; A61J 1/10; A61J 1/16; B01D 21/262
USPC ............................................... 494/15, 21, 83

See application file for complete search history.

(56) References Cited

U.S. PATENT DOCUMENTS

| 4,720,284 | A | 1/1988 | McCarty | |
|---|---|---|---|---|
| 6,910,998 | B2 | 6/2005 | Eberle | |
| 2008/0304781 | A1* | 12/2008 | Hofmann | ................ F16C 19/26 |
| | | | | 384/558 |
| 2012/0171068 | A1* | 7/2012 | Steffens | .................. F04C 29/04 |
| | | | | 418/91 |
| 2019/0353230 | A1* | 11/2019 | Kajihara | ............. F16H 25/2204 |
| 2020/0088244 | A1* | 3/2020 | Ryba | ........................ F16D 23/12 |
| 2020/0391988 | A1* | 12/2020 | Siemens | ............. F16C 35/0635 |

OTHER PUBLICATIONS

PCT International Preliminary Report on Patentability dated Sep. 29, 2022 in counterpart PCT Application No. PCT/EP2021/058069 (1 page in English).
PCT International Search Report dated Jul. 2, 2021 issued in counterpart PCT Application No. PCT/EP2021/058069 (2 pages in English).

* cited by examiner

INSERT FOR A CENTRIFUGE ROTOR HAVING LUBRICANT-FREE BEARING

The present application is a National Stage application of PCT International Application No. PCT/EP2021/058069, filed on Mar. 29, 2021, the disclosure of which is hereby incorporated by reference in its entirety.

The invention relates to an insert for a rotor, which can be rotated about a rotor axis, of a centrifuge, said insert being of the type specified in the preamble of claim 1.

Such inserts for centrifuge rotors have been known for some time and are used for the automated separation as well as the separation integrated within the centrifuge, of for example red blood cells from blood plasma in a process bag of a blood bag system. A process bag of a blood bag system filled with donor blood is used in such an insert, for example. The process bag contains the pre-filtered blood donation, for example. The blood bag system has one or more satellite bags, for example, that may be empty or pre-filled with a culture medium. The satellite bags and the process bag are connected to one another via plastic tubings. During centrifugation, the red blood cells—RBC—and the blood plasma—PPP—settle on the outer rim according to their respective density. Sedimentation takes place at 2,500 rpm (revolutions per minute) of the centrifuge rotor, so that the red blood cells, which are denser, will accumulate towards the outside of the interior of the process bag, and the less dense blood plasma will settle further inside.

The insert is provided with a housing comprising a process container for the process bag as part of the housing and further containers for the satellite bags. A slider is arranged in the container for the process bag, which slider is adapted to be extended radially, with respect to a rotor axis, against the process bag and retracted again. For this purpose, the slider is connected to a drive that cooperates with a rotatable spindle nut and a spindle. The spindle nut is rotatably mounted in the housing of the insert. The spindle passes through the spindle nut, is translationally slidably mounted in the spindle nut and is non-rotatably connected to the slider.

As has been explained, the slider is mounted in the process container and acts on the process bag in a predetermined manner, in that the spindle, and thus via it the slider, is moved between a starting position and an operating position in the direction toward and away from the rotor axis. The spindle nut is rotatably mounted in the housing of the insert via at least one bearing and serves as a means to convert the rotational motion initiated by the drive into a translational motion.

Since heat is generated during centrifugation, which, however, has a detrimental effect on the red blood cells and blood plasma since blood cells and blood plasma may become unusable, the rotor chamber of the centrifuge, in which the rotor with the insert(s) is located, is cooled. Cooling of the rotor chamber is therefore intended to prevent the red blood cells and blood plasma from heating up by all means.

For separating the blood plasma from the red blood cells, the slider is pressed against the process bag via the spindle at a low centrifuge speed, for example in the 300 rpm to 600 rpm range, and thereby displaces the blood plasma in the process bag from it. Via the connected plastic tubing, which is held in place in particular in and on the insert by integrated tube clamps, together with an optical detection system, the blood plasma is thus pressed into the one or plural associated satellite bag(s). The red blood cells then remain in the process bag, for example. This pressing process by moving the slider onto the process bag takes place under the effect of centrifugal force, i.e. during operation of the centrifuge, among other things in order to stabilize the individual layers in the process bag.

The problem with the inserts known from the prior art is that the process bags, but also the satellite bags, can become contaminated, especially by the moving parts of the insert, for example by abrasion or rust produced during operation and/or by lubricants, with the result that only part of the blood plasma and of the red blood cells is still usable, or they become unusable in their entirety. Rust may be caused by the cooling and the associated condensation of the air in the rotor chamber. Lubricant and abrasion can come from the parts moving relative to each other and may deposit on the bag system as a result of centrifugal forces. As a result of diffusion processes through the bags, the blood samples, blood cells and blood plasma may become contaminated.

It is the object of the invention to improve on an insert for a rotor of a centrifuge of the type specified in the preamble term of claim 1 in such a way that contamination of the bags of the bag system, i.e. the process bags and possibly the satellite bags, can almost completely be eliminated.

This object is accomplished by the characterizing features of claim 1 in conjunction with the features of its preamble.

The dependent claims relate to advantageous further embodiments of the invention.

The invention is based on the insight that the bearing for the slider is a major source of potential contamination within the insert and bag system, for which reason measures to limit contamination must start here. It has been shown that contamination can be significantly reduced, in particular by using a lubricant-free bearing.

According to the invention, the bearing is therefore constituted by a lubricant-free bearing having an outer bearing ring in contact with the housing and a bearing ring in contact with the spindle nut.

This is a simple way to prevent lubricant from escaping and contaminating the bags of the bag system.

In addition, in order to avoid contamination by rust in particular, a stainless bearing is used. Consequently, condensation will no longer have any influence on rust formation in the bearing.

However, since the spindle nut in the bearing moves during centrifugation to press the blood plasma into the satellite bags, the bearing must additionally withstand the forces that occur during centrifugation. It is therefore advantageous for the bearing to be constituted by a rolling bearing which is capable of absorbing higher forces.

However, the problem with rolling bearings is that they cause abrasion. In one embodiment of the invention, the bearing is therefore formed by a hybrid bearing. Hybrid bearings are almost completely abrasion-free. The rolling elements can be made of ceramic, and the outer ring and inner ring can be made of stainless steel.

In order to also protect the bag system and the rest of the insert from minor abrasion, the bearing is formed by a sealed, encapsulated, in particular a plastic-encapsulated, rolling bearing.

The outer ring and/or the inner ring of the rolling bearing can be of a single-part or a multi-part design. For the centrifugal forces acting in the centrifuge, it is advantageous, with regard to bearing stability, for the outer ring and/or the inner ring of the rolling bearing to be formed in one piece.

Especially when only one bearing is used, it is considered favorable for the bearing to be designed as a four-point bearing. Four-point bearings are, for example, single-row radial angular contact ball bearings whose raceways are designed to support axial loads in both directions. Radial loads can only be absorbed up to a fraction of the axial load.

Preferably, the bearing has nine rolling elements.

In one embodiment of the invention, the axis of rotation of the bearing is on a radial line of the rotor axis. In this way, any potential imbalances are avoided during the process.

To further limit the spread of rust, abrasion and the like, some areas of the bearing are enclosed by the housing, the spindle nut, a clamping element, a fixing plate and another seal.

In one embodiment of the invention, an outer seal is fitted to the bearing on the side of the bearing facing away from the rotor axis, which seal acts to seal a bearing gap between the housing and the spindle nut. The seal prevents contaminated substances from escaping through the outer seal.

Preferably, the housing is provided with a wall on which the bearing is arranged. In addition, the drive has a motor and a first gear unit connected to the motor. The motor and the first gear unit are located on the one side of the wall, and the slider is located on the other side of the wall. The wall can be used as an easy means to separate the slider acting on the bag system from most of the moving parts. In addition, the wall serves to receive the outer ring of the bearing and can form the rear wall of the container.

In order to transmit the drive force from the motor to the spindle nut via the first gear unit, the drive has a second gear unit which is connected to both the first gear unit and to the spindle nut, the second gear unit being located on the same side as the slider.

The drive can be arranged closer to the rotor axis than the slider. This is also favorable in that the moving masses are then closer to the rotor axis, resulting in more stable running of the centrifuge.

The wall may have a shoulder for accommodating the bearing. In this case, the bearing is inserted into the shoulder with the outer ring of the bearing from the side that is closer to the rotor axis. This ensures that there is already a separation between the bearing on the one side and the slider in the container for the blood bag system on the other side.

The spindle nut may have a shoulder to receive the bearing. In this case, the bearing is inserted into the shoulder with the inner ring of the bearing from the side that is closer to the rotor axis. Installation is thus carried out from the side of the wall facing away from the slider. This is a simple way of structurally separating the moving parts of the drive with the bearing on the one side from the slider on the other side.

Preferably, on the side of the housing remote from the shoulder of the wall, the outer ring is connected to the wall of the housing in the axial direction by a fixing element, in particular a fixing plate, which is connected to the wall of the housing, in particular in a releasable manner.

The inner ring can be connected to the spindle nut in the axial direction on the side remote from the shoulder of the spindle nut by a clamping element, in particular by a clamping ring mounted on the spindle nut or a threaded nut mounted on the spindle nut.

In addition, an inner seal can be provided between the fixing element and the clamping element in order to seal the bearing gap between the fixing plate and the clamping nut. This allows further separation of contaminating substances from the container with the slider in a simple way.

Additional advantages, features and possible applications of the present invention will be apparent from the description which follows, in which reference is made to the embodiments illustrated in the drawings.

Throughout the description, the claims and the drawings, those terms and associated reference signs are used as are stated in the list of reference signs below. In the drawings, FIG. 1 is a perspective view, as seen at an angle from above, of a centrifuge with its lid open and having inserts according to the invention installed in the rotor;

Illustrated in FIGS. 1 to 7 is an embodiment of an insert 10 for a rotor 14, which can be rotated about a rotor axis 12, of a centrifuge 16.

Figure 1:
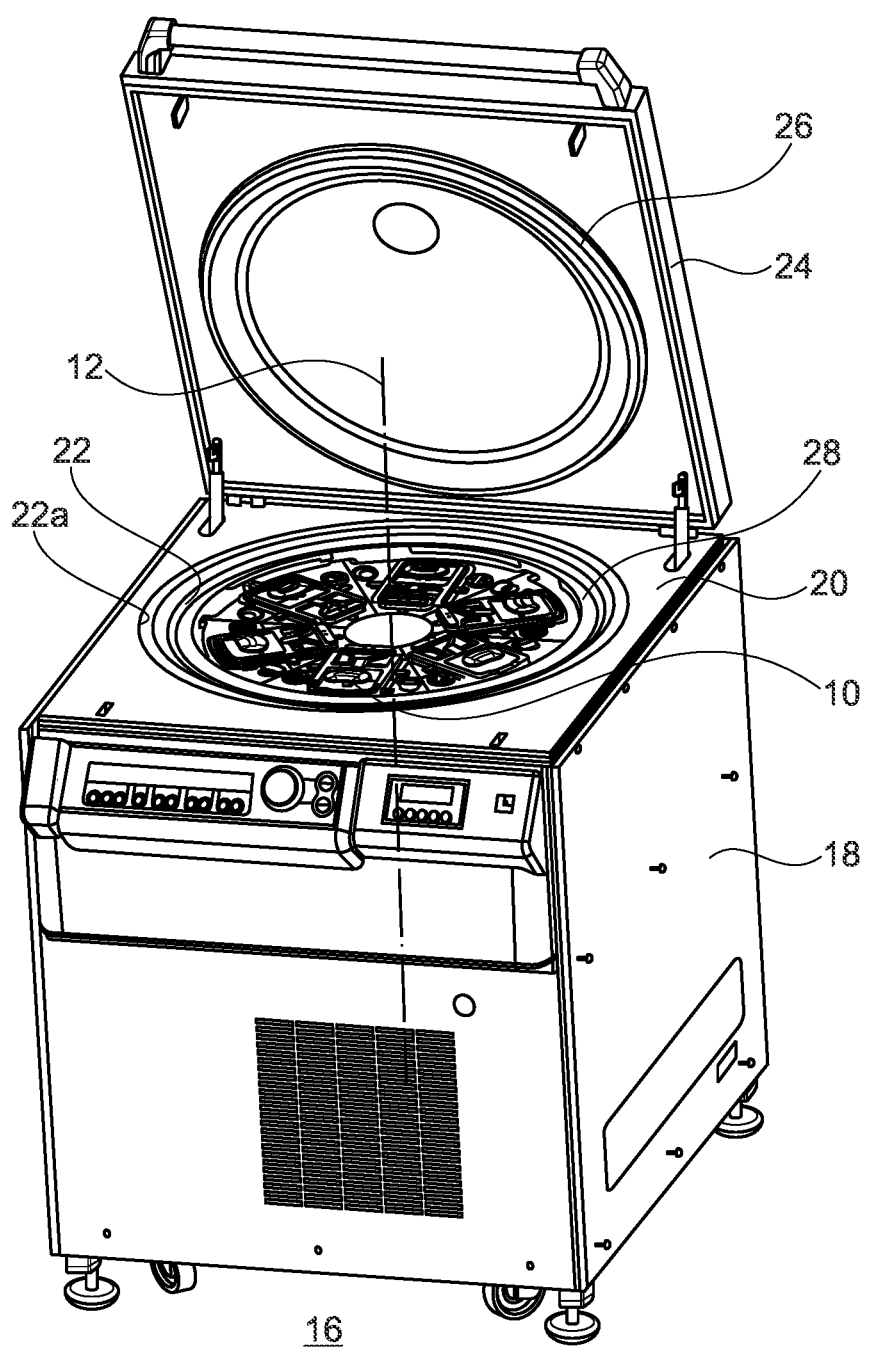

As can be seen from FIG. 1, the centrifuge 16 is provided with a closed housing 18 which has a circular loading opening 22 in its top ceiling wall 20. The loading opening 22 may be closed by a cover 24 hinged to the housing 18. For this purpose, the cover 24 has a sealing ring 22a adapted to the loading opening 22 and arranged in alignment with this loading opening 22. When the cover 24 is closed, the sealing ring 22a engages an annular shoulder 26 of the loading opening 22 and tightly closes the loading opening 22 in this way.

Figure 2:
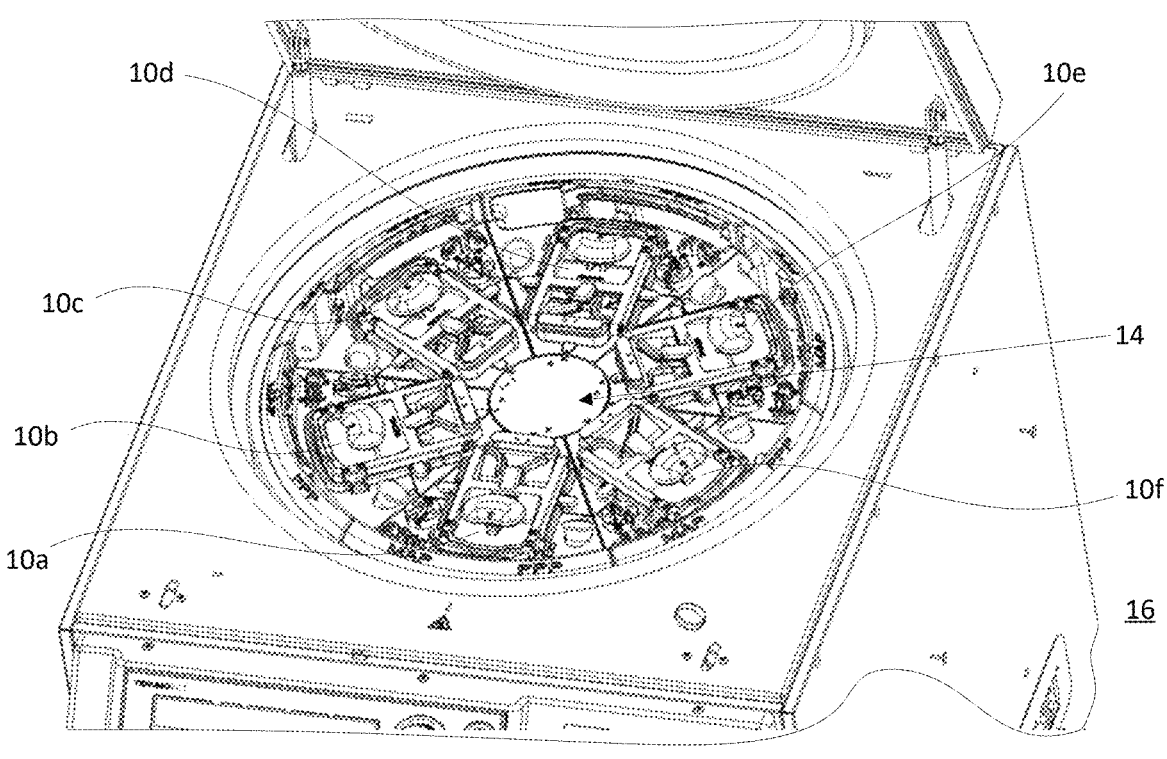
FIG. 2 is a perspective detail view, as seen at an angle from above, of the inserts of FIG. 1 installed in the rotor.
Figure 3:
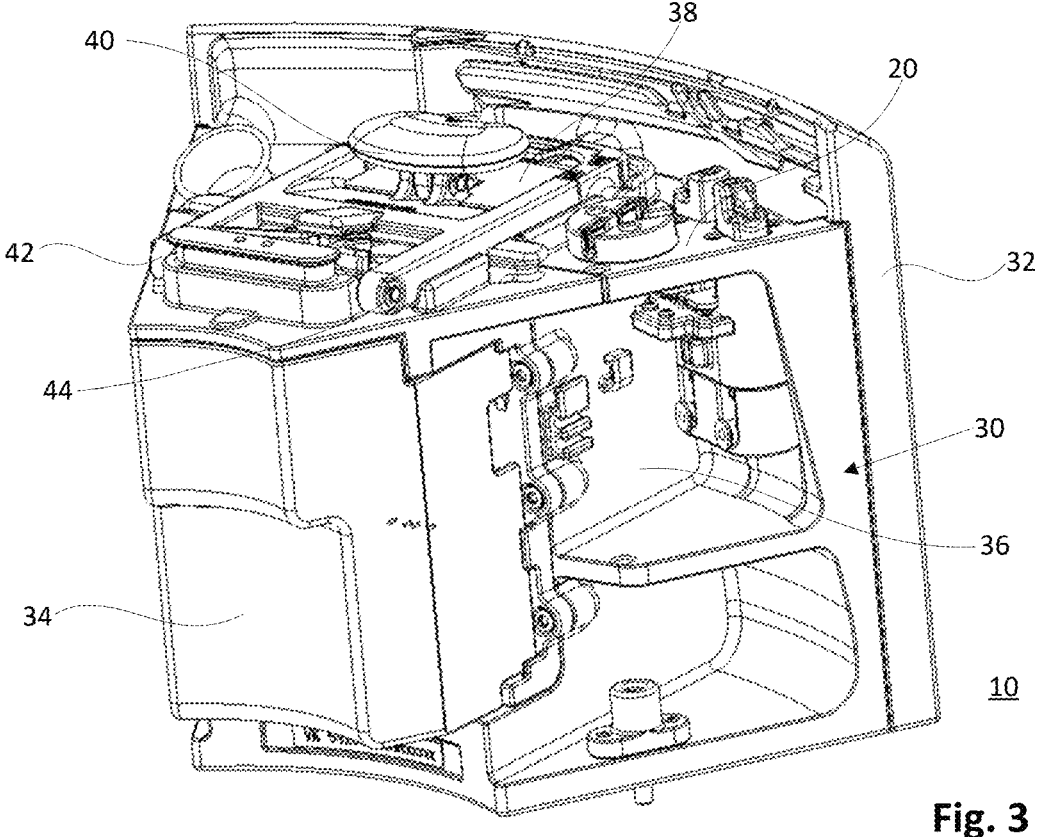
FIG. 3 is a perspective view of an insert that has been removed from the rotor.

When the lid 24 is open, the loading opening 22 allows loading of the rotor 14, which has six inserts 10a to 10f according to the invention installed in it, see FIG. 2. The rotor 14 with the inserts 10 is arranged in a cooled rotor chamber 28. All six inserts 10a to 10f are of the same structure, so that the description of one insert 10 applies to all inserts 10a to 10f.

As can be seen from FIGS. 3 to 7, an insert 10 includes a housing 30. The housing 30 is provided with an outer wall 32 and an inner cover 34, which delimit the housing radially outwardly and inwardly, respectively. In addition, the housing 30 includes a process container 36 that is closed by a process container lid 38 with a handle 40. In the upper portion of the process container 36, the process container lid 38 is connected to an upper insert wall 46 of the housing 30 of the insert 10 by first and second joints 42, 44.

Figure 4:
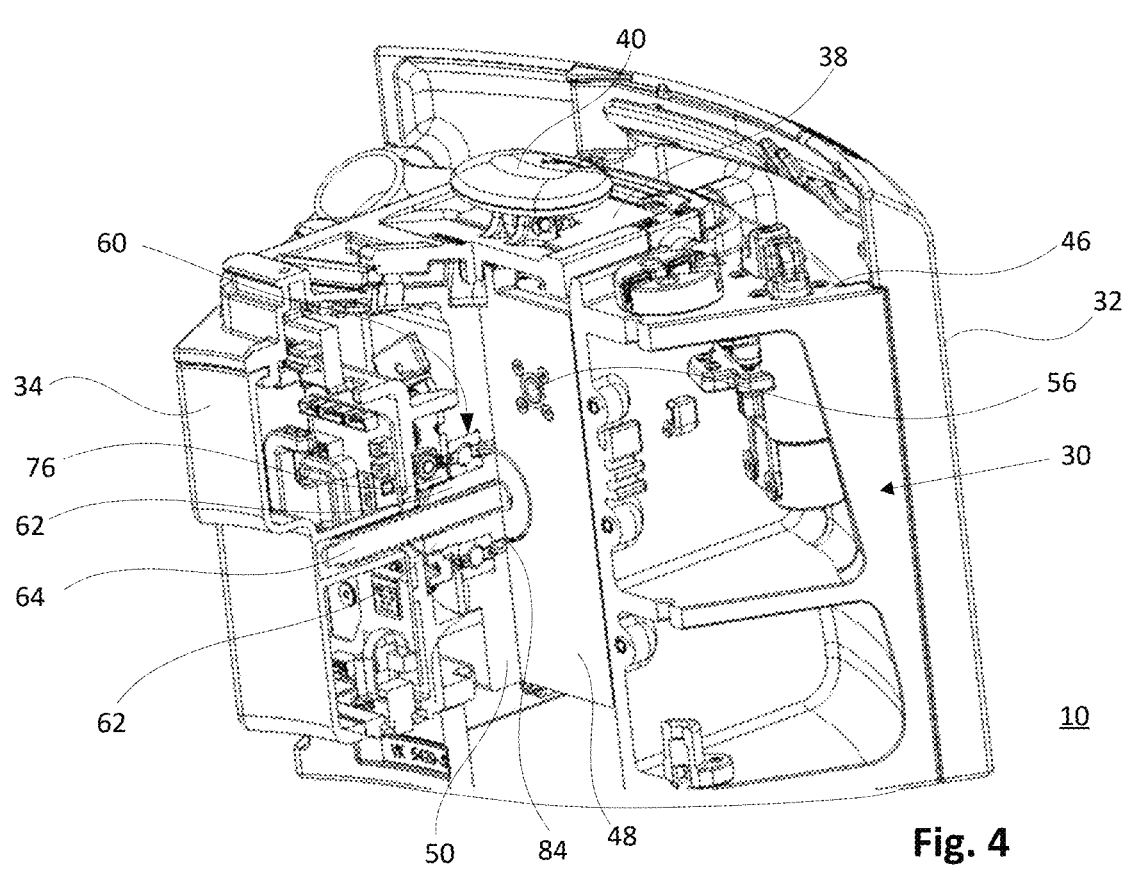
FIG. 4 is a perspective view of the insert of FIG. 3 with a partial section through the inner area of the insert in the area of the inner cover.
Figure 5:
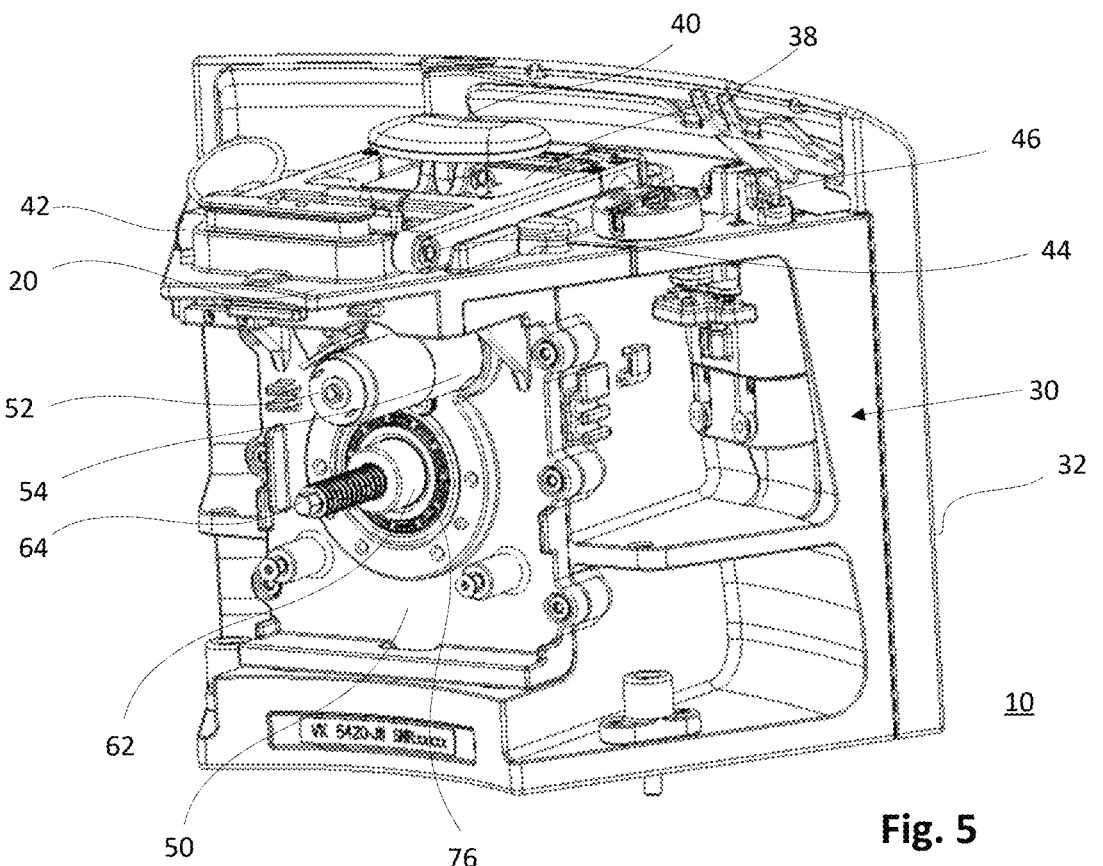
FIG. 5 is a perspective view of the insert of FIG. 3 without an inner cover and with other internals.
Figures 6, 7:
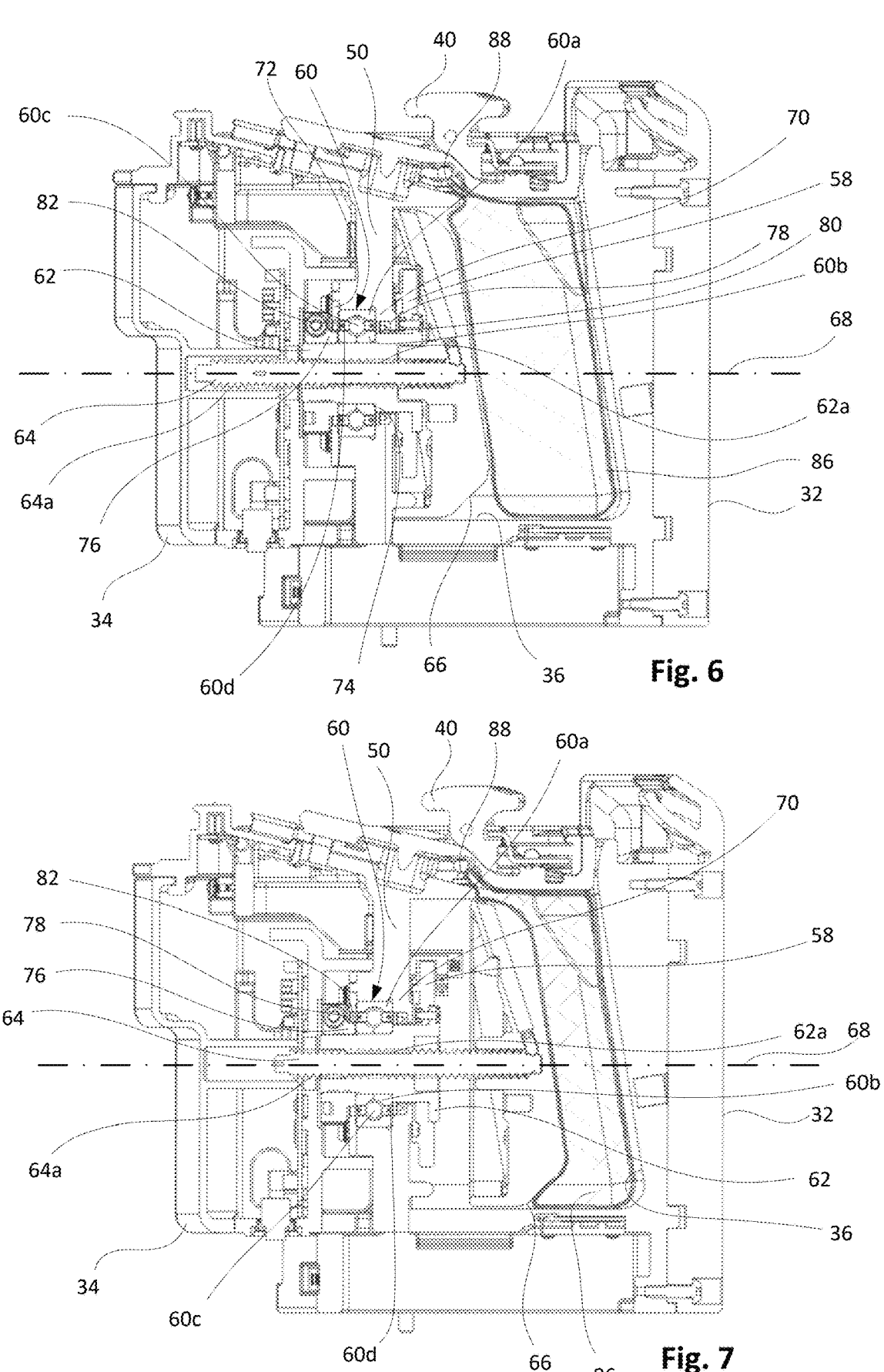
FIG. 6 is a side sectional view through the insert along an axis of rotation of a spindle nut of the insert, showing a slider in its retracted state and a process bag inserted into a container.
FIG. 7 is a side sectional view similar to that of FIG. 6, but with the slider in its extended state.

Adjacent to a rear wall 48 of the process container 36 is a supporting wall 50 which is screw-connected to the side of the housing 30 in the area of the rear wall 48 of the process container 36, see FIG. 4 and FIG. 5. The rear wall 48 and the supporting wall 50 may also be identical, as shown in FIGS. 6 and 7.

A motor 52 and a first gear unit 54 are fixed to the supporting wall 50. A drive spindle (not shown here) extends through an opening 56, see FIG. 4, and connects the first gear unit 54 with a second gear unit 58, see FIGS. 6 and 7. The second gear unit 58 is connected to a spindle nut 62 which is mounted so as to be rotatable in a bearing 60 in the supporting wall 50, thus allowing the spindle nut 62 to be driven via the motor 52, the first gear unit 54 of the drive spindle (not shown here) and the second gear unit 58.

An axially displaceable spindle 64 is mounted in the spindle nut 62, which has a thread 64a on its outside in which an internal thread 62a of the spindle nut 62 engages. The spindle 64 is non-rotatably connected to a slider 66. Rotation of the spindle nut 62 causes the spindle, and thus also the slider 66, to be axially displaced via the engaging internal thread 62a of the spindle nut 62 and the external thread 64a of the spindle 64. Depending on the direction of rotation, there is an axial displacement of the spindle 64 away from or towards the rotor axis 12. The axis of rotation of the spindle nut 62 and the longitudinal axis of the spindle 64 form a common axis 68, which extends radially away from the rotor axis 12.

The spindle nut 62, in cooperation with the spindle 64, thus serves as a motion converter for converting a rotational motion introduced into the spindle nut 62 by the motor 52, the first gear unit 54, and the second gear unit 58 into a translational motion of the spindle 64 and thus of the slider 66.

The spindle 64 protrudes far into the space delimited by the inner cover 34 and thus projects from the spindle nut 62 because the slider 66 is in its starting position, see FIG. 4, FIG. 5 and FIG. 6.

The bearing 60 is a lubricant-free, stainless steel rolling bearing, namely a four-point hybrid bearing. The bearing 60 has its outer ring 60a abutting a shoulder 70 of the supporting wall 50. The outer ring 60a is fixed without play in the axial direction in the shoulder 70 by a fixing plate 72 fixed to the supporting wall 50 on the side facing away from the process container 36. Furthermore, the bearing 60 has its inner ring 60b resting against an outer shoulder 74 of the spindle nut 62. A clamping ring 76 is used to firmly clamp the inner ring 60b in the direction of the outer shoulder 74.

In the views of FIG. 6 and FIG. 7, a split inner ring 60b was used for the bearing 60. However, it is more convenient to use a single-piece inner ring 60b.

Mounted between the outer ring 60a and the inner ring 60b are nine rolling elements in the form of rolling balls 60c. The bearing 60 is terminated with a bearing housing 60d disposed to the left and right of the rolling balls 60c and between the outer ring 60a and the inner ring 60b. The bearing housing 60d is made of plastic and seals the bearing 60 so that no abrasion can escape to the outside.

The outer ring 60a and the inner ring 60b are made of stainless steel, in particular X1005CrMo17. The rolling balls 60c are made of ceramic, in particular Si3N4.

As can be seen in particular from FIG. 6 and FIG. 7, a bearing gap 78 located in the region of the shoulder 70 of the supporting wall 50 is sealed by an outer seal 80. In this way, the encapsulated bearing 60 is further enclosed/encapsulated by the supporting wall 50, the outer seal 80, the spindle nut 62, as well as the clamping ring 76 and the fixing plate 72.

Furthermore, an additional seal 82 may also be provided between the fixing plate 72, the clamping ring 76 and the inner ring 60b.

The shoulder 70 of the supporting wall 50 and the outer shoulder 74 of the spindle nut 62 are arranged so that the bearing 60 is mounted from the side of the supporting wall 50 that is closest to the rotor axis 12.

The spindle nut 62, on the other hand, is inserted from the side of the supporting wall 50 and the rear wall 48 of the process container 36 into an associated opening 84, which is remote from the rotor axis 12.

The inner cover 34 is placed on the supporting wall 50 from the side of the supporting wall 50 that faces the rotor axis 12 and is releasably connected to it by means of a click mechanism (not shown in more detail here).

As seen in FIGS. 6 and 7, a process bag 86 of a bag system has each been placed in the process container 36. This process bag 86 is filled with donor blood. FIG. 6 shows the slider 66 in its starting position. Plastic tubing 88 connects the process bag 86 to satellite bags (not shown here). In this starting position of the slider 66, centrifugation starts by rotating the rotor 14. This process causes the red blood cells—RBC—and the blood plasma—PPP—to deposit on the outer edge according to their respective density. Sedimentation takes place at a speed of 2,500 rpm (revolutions per minute) of the rotor 14 of the centrifuge 16, causing the red blood cells, which are of higher density to deposit toward the outside inside the process bag 86, with the blood plasma of lesser density, to be deposited further towards the inside. Once separation is fully completed, the blood plasma is removed from the process bag 86.

For this purpose, the motor 52 is started and drives the spindle nut 62 via the first gear unit 54 and the second gear unit 58. Subsequently, the spindle 64, which is connected to the slider 66, is caused to move translationally from its starting position as shown in FIG. 6 towards its operating position, and, along with the spindle 64, so is the slider 66.

In order to move the blood plasma out of the process bag 86 that contains the red blood cells, without, however, entraining the red blood cells, the slider 66 is successively pressed against the process bag 86 via the spindle 64 in the manner described, at a low speed of the centrifuge 16, for example in the range of between 300 rpm and 600 rpm. This causes the blood plasma in the process bag 86 to be displaced from it. Via the connected plastic tubing 88, which is held in and on the insert by integrated tube clamps (not shown here), together with an optical detection system which interacts with a controller/control unit, the blood plasma is pressed into the associated one or plural associated satellite bag(s). This ensures that the red blood cells remain in the process bag. This process of pressing the blood plasma into the satellite bag by means of the movement of the slider 66 occurs under the action of centrifugal force, i.e. during operation of the centrifuge 16, among other things to stabilize the individual layers in the process bag 86.

According to the invention, the bearing 60, which is a potential source of contaminants, is largely designed such that no contaminants are present in the first place and will not be produced either. In addition, the bearing 60 is enclosed/encapsulated in stages so that, in any event, contaminants are prevented from entering the process container 36 and thus from being introduced into the process bag 86. Contamination of the substances contained in the process bag 86, for example blood donations, is thus effectively prevented in a simple manner.

LIST OF REFERENCE SIGNS 10 insert
10a first insert
10b second insert
10c third insert
10d fourth insert
10e fifth insert
10f sixth insert
12 rotor axis
14 rotor
16 centrifuge
18 housing
20 upper ceiling wall of centrifuge housing
22 loading opening
22a sealing ring
24 lid
26 annular shoulder

28 rotor chamber
30 housing of insert 10
32 outer wall
34 inner cover
36 process container
38 process container lid
40 handle
42 first joint
44 second joint
46 upper insert wall 46 of housing 30 of insert 10
48 rear wall of process container 36
50 supporting wall
56 opening
58 second gear unit
60 bearing
60a outer ring of bearing 60
60b inner ring of bearing 60
60c rolling elements of bearing 60
60d bearing housing of bearing 60
62 spindle nut
62a internal thread of spindle nut 62
64 spindle
64a external thread of spindle 64
66 slider
68 axis
70 shoulder of supporting wall 50
72 fixing plate
74 outer shoulder of spindle nut 62
76 clamping ring
78 bearing gap
80 outer seal
82 additional seal, inner seal
84 opening for spindle nut in supporting wall 50 and rear wall 48 of process container 36
86 process bag
88 plastic tubing

The invention claimed is:

1. An insert for a rotor, which can be rotated about a rotor axis, of a centrifuge comprising a housing having at least one container for bags, comprising a slider that cooperates with a drive, a rotatable spindle nut and a spindle, wherein the spindle nut is rotatably mounted in the housing and connected to the drive, and the spindle is translationally slidably mounted in the spindle nut and connected to the slider, wherein the slider is arranged in the container and acts on the bag in a predetermined manner, in that the spindle can be moved between a starting position and an operating position, wherein the spindle nut is rotatably mounted in the housing via at least one bearing, wherein the bearing is formed by a lubricant-free bearing having an outer bearing ring in contact with the housing and an inner bearing ring in contact with the spindle nut, and wherein the housing comprises a wall in which the bearing is arranged, the drive comprises a motor and a first gear unit connected to the motor, the motor and the first gear unit are arranged on one side of the wall and the slider is arranged on the other side of the wall.

2. An insert according to claim 1, wherein the bearing is a stainless steel bearing.

3. An insert according to claim 1, wherein the bearing is a rolling bearing.

4. An insert according to claim 3, wherein the bearing is formed by a hybrid bearing.

5. An insert according to claim 3, wherein the bearing is formed by a sealed, encapsulated rolling bearing.

6. An insert according to claim 5, wherein the bearing is plastic encapsulated.

7. An insert according to claim 3, wherein at least one of the outer ring and the inner ring of the rolling bearing are formed as one piece.

8. An insert according to any claim 3, wherein the bearing is a four-point bearing.

9. An insert according to claim 3, wherein the bearing has nine rolling elements.

10. An insert according to claim 1, wherein the axis of rotation of the bearing lies on a radial line of the rotor axis.

11. An insert according to claim 1, wherein areas of the bearing are enclosed by the housing, the spindle nut, a clamping element such as a clamping ring, a fixing element such as a fixing plate, and a seal.

12. An insert according to claim 1, wherein an outer seal adjoins the bearing on the side of the bearing that faces away from the rotor axis and seals a bearing gap between the housing and the spindle nut.

13. An insert of claim 1, wherein the drive comprises a second gear unit connected to both the first gear unit and the spindle nut, which second gear unit is located on the same side relative to the wall as the slider.

14. An insert according to claim 1, wherein, with respect to the slider, the drive is arranged closer to the rotor axis.

15. An insert according to claim 1, wherein the wall has a shoulder for receiving the bearing, and that the bearing is inserted into the shoulder with the outer ring of the bearing from the side which is closer to the rotor axis.

16. An insert according to claim 15, wherein the spindle nut has a shoulder for receiving the bearing, and that the bearing is inserted into the shoulder with the inner ring of the bearing from the side which is closer to the rotor axis.

17. An insert according to claim 15, wherein on the side of the housing remote from the shoulder of the wall, the outer ring is connected in the axial direction to the wall of the housing by a fixing element, which is connected to the wall of the housing.

18. An insert according to claim 17, wherein the fixing element is a fixing plate, which is releasably connected to the wall of the housing.

19. An insert according to claim 16, wherein on the side remote from the shoulder of the spindle nut, the inner ring is connected in the axial direction to the spindle nut by a clamping element mounted on the spindle nut.

20. An insert according to claim 17, wherein an inner seal is provided between the fixing element and the clamping element, which inner seal acts to seal the bearing gap between the fixing plate and a clamping element.

* * * * *